United States Patent
Degala et al.

(10) Patent No.: US 9,895,455 B2
(45) Date of Patent: Feb. 20, 2018

(54) SYSTEMS, METHODS, AND DEVICES FOR STERILIZING ANTISEPTIC SOLUTIONS

(71) Applicant: CAREFUSION 2200, INC., San Diego, CA (US)

(72) Inventors: Satish Degala, Arlington Heights, IL (US); Christopher Matthew McGinley, Highland Park, IL (US); Kenneth Bruce Thurmond, Deer Park, IL (US); Taryn Bagby, St. Peters, MO (US)

(73) Assignee: Carefusion 2200, Inc, San Diego, CA (US)

( * ) Notice: Subject to any disclaimer, the term of this patent is extended or adjusted under 35 U.S.C. 154(b) by 0 days.

(21) Appl. No.: 14/788,316

(22) Filed: Jun. 30, 2015

(65) Prior Publication Data
US 2017/0000914 A1   Jan. 5, 2017

(51) Int. Cl.
A61L 11/00   (2006.01)
A61L 2/00   (2006.01)
A61L 2/04   (2006.01)

(52) U.S. Cl.
CPC .............. *A61L 2/04* (2013.01); *A61L 2202/21* (2013.01)

(58) Field of Classification Search
CPC ... A61L 2/00; A61L 2/186; A61L 2/04; B65D 81/32
USPC ....................................................... 422/1, 38
See application file for complete search history.

(56) References Cited

U.S. PATENT DOCUMENTS

| | | |
|---|---|---|
| 4,106,654 A | 8/1978 | Jones |
| 4,438,011 A | 3/1984 | Howes |
| 4,646,629 A | 3/1987 | Creed et al. |
| 7,868,016 B2 | 1/2011 | Singh et al. |
| 8,062,649 B2 | 11/2011 | Asmus et al. |
| 8,110,144 B2 | 2/2012 | Morales |
| 8,383,038 B2 | 2/2013 | Kitano |
| 2007/0178051 A1 | 8/2007 | Pruitt et al. |
| 2008/0139519 A1 | 6/2008 | Ashley et al. |

(Continued)

FOREIGN PATENT DOCUMENTS

| | | |
|---|---|---|
| CN | 102993056 A | 3/2013 |
| CN | 103202827 A | 7/2013 |

OTHER PUBLICATIONS

Dictionary.com definition of bottle; http://dictionary.reference.com/browse/bottle; accessed Apr. 30, 2015.

(Continued)

*Primary Examiner* — Monzer R Chorbaji
(74) *Attorney, Agent, or Firm* — Arent Fox LLP

(57) ABSTRACT

A method for sterilizing an aqueous antiseptic solution, the method comprising providing a container containing the aqueous antiseptic solution, the aqueous antiseptic solution comprising a bis-(dihydropyridinyl)-decane derivative or a biguanide, heating the aqueous antiseptic solution to a predetermined temperature, maintaining the aqueous antiseptic solution at the predetermined temperature for a predetermined time, and terminating the heating of the aqueous antiseptic solution when the predetermined time expires. The predetermined temperature and the predetermined time are selected such that after terminating the heating, the aqueous antiseptic solution is sterile.

21 Claims, 3 Drawing Sheets

(56) References Cited

U.S. PATENT DOCUMENTS

2013/0094995 A1\* 4/2013 Koyama ................ A61L 2/186
                                                        422/28
2014/0322072 A1   10/2014 Margoosian et al.
2015/0217008 A1    8/2015 Zwingenberger et al.

OTHER PUBLICATIONS

International Search Report dated Apr. 13, 2015 issued in International Patent Application No. PCT/US15/10465.
Small, H. et al., "Efficacy of adding 2 percent (w/v) chlorhexidine gluconate to 70 percent (v/v) isopropyl alcohol for skin disinfection prior to peripheral venous cannulation", Infection Control and Hospital Epidemiology, vol. 29, pp. 963-965; abstract; title (2008).
Adams et al. "Evaluation of a 2% chlorhexidine gluconate in 70% isopropyl alcohol skin disinfectant", Journal of Hospital infection, Elsevier, Amsterdam, NL, vol. 61, No. 4, Dec. 1, 2005, pp. 287-290.
Yoshiyuki Kawaga et al. "Heat-resistant Properties in Autoclaving of new Polycarbonate Bottles Containing a Disinfectant of Chlorohexidine Digluconate Solution", Jpn. J. Hosp. Pharm., vol. 20, No. 5, 1994, pp. 361-367.

\* cited by examiner

SYSTEMS, METHODS, AND DEVICES FOR STERILIZING ANTISEPTIC SOLUTIONS

FIELD OF THE INVENTION

Aspects of the present invention relate to the field of sterilization, and in particular, to sterilization of topical antiseptic solutions.

BACKGROUND OF THE INVENTION

In the United States there are currently no regulations regarding the sterilization requirements of topical antiseptic solutions. Therefore, antiseptic solutions currently sold in the United States generally do not undergo a sterilization process. In other jurisdictions, however, such as European Union (EU) countries, some degree of sterilization is required. A known antiseptic solution containing 2% w/v chlorhexidine gluconate in 70% v/v isopropanol in water (i.e., an alcoholic solution), manufactured by CareFusion Corp., is sterilized for EU countries using a known sterilization method.

It is the industry belief that high temperature sterilization is not suitable due to the expected degradation. See, for example, Kelly M. Pyrek, "Sterility of Antiseptic Products: FDA Investigates, Deliberates on Potential Recommendations," *Infection Control Today* (July 2013): 24-26 and Block, Seymour S. *Disinfection, Sterilization, and Preservation*. Philadelphia: Lippincott Williams & Wilkens, 322-323. 2001.

A known method of sterilization involves heat treating glass ampoules containing the chlorhexidine gluconate alcoholic solution in a convection oven at 76-80° C. for 24-31 hours. It was believed that relatively low temperature and relatively long processing time is necessary to sufficiently sterilize the antiseptic alcoholic solution without overly degrading the antimicrobial molecules, thereby avoiding reducing the concentration and purity of the chlorhexidine gluconate contained therein as an antiseptic. Applicant's copending U.S. application Ser. No. 14/150,488 describes an alternative method for sterilizing an alcoholic solution, which is hereby expressly incorporated by reference herein in its entirety.

However, there is no known method of sterilizing an aqueous antiseptic solution that affords a sterile solution without overly degrading the antimicrobial molecules. Thus, there is an unmet need in the art for a method of sterilizing aqueous antiseptic solutions.

SUMMARY OF THE INVENTION

Aspects of the present invention overcome the above identified problems, as well as others, by providing systems, methods, and devices for efficiently sterilizing antimicrobial solutions while maintaining antimicrobial efficacy as an aqueous antiseptic and purity of the active drug moiety to comply with regulatory requirements.

A method for sterilizing an aqueous antiseptic solution, the method comprising providing a container containing the aqueous antiseptic solution, the aqueous antiseptic solution comprising a bis-(dihydropyridinyl)-decane derivative or a biguanide, heating the aqueous antiseptic solution to a predetermined temperature, maintaining the aqueous antiseptic solution at the predetermined temperature for a predetermined time, and terminating the heating of the aqueous antiseptic solution when the predetermined time expires. The predetermined temperature and the predetermined time are selected such that after terminating the heating, the aqueous antiseptic solution is sterile.

In another example aspect, the sterilization temperature and the sterilization time are selected such that after terminating the heating, the antiseptic solution has a post-sterilization purity of at least about 90% and the percentage point change in purity from the initial purity to the post-sterilization purity is at most about 8%.

In another example aspect, the antiseptic solution comprises water and about 2.0% w/v chlorhexidine gluconate.

In another aspect, the sterilization temperature is about 100° C. and the sterilization time is from about 20 minutes to about 33 hours. In an another example aspect, the sterilization temperature is about 110° C. and the sterilization time is from about 6 minutes to about 11 hours. In another aspect, the sterilization temperature is about 115° C. and the sterilization time is from about 3.5 minutes to about 6 hours. In another aspect the sterilization temperature is about 125° C. and the sterilization time is from about 1 minute to about 2 hours.

In another example aspect, the selected sterilization temperature and the selected sterilization time are chosen such that after terminating the heating, the antiseptic solution has a post-sterilization purity of at least about 93% and the percentage point change in purity from the initial purity to the post-sterilization purity is at most about 5%.

In another example aspect, the selected sterilization temperature and the selected sterilization time are chosen such that after terminating the heating, the antiseptic solution has a post-sterilization purity of at least about 95% and the percentage point change in purity from the initial purity to the post-sterilization purity is at most about 3%.

Additional advantages and novel features relating to aspects of the present invention will be set forth in part in the description that follows, and in part will become more apparent to those skilled in the art upon examination of the following or upon learning by practice thereof.

DETAILED DESCRIPTION

Figure 1:
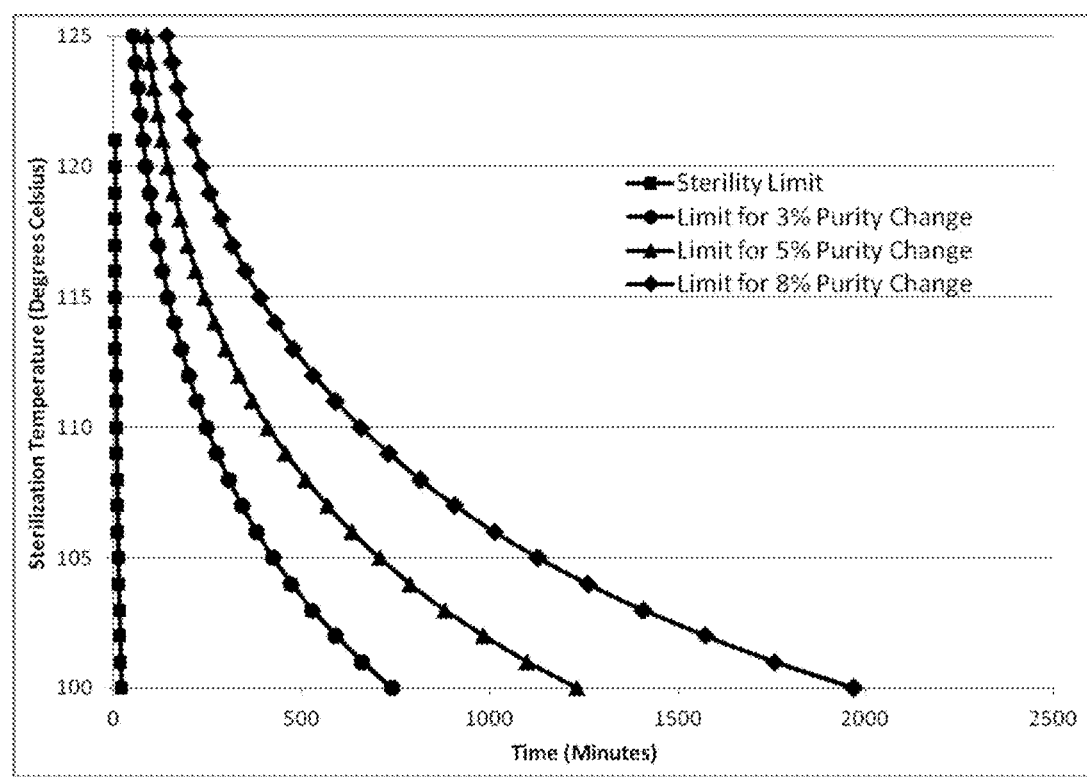
FIG. 1 is a graph of sterilization temperature and sterilization time data in accordance with certain aspects of the present invention.

Aspects of the present invention overcome the above identified problems, as well as others, by providing systems, methods, and devices for sterilizing an aqueous antiseptic solution while maintaining antimicrobial efficacy and while complying with regulatory requirements.

Various aspects of an antiseptic applicator may be illustrated with reference to one or more exemplary embodiments. As used herein, the term "exemplary" means "serving as an example, instance, or illustration," and should not necessarily be construed as preferred or advantageous over other embodiments of sterilization methods disclosed herein.

The term "about" as used herein preferably means ±5% and more preferably ±1% of the provided value.

Aspects of the present invention include a method of sterilizing aqueous antiseptic solution contained in a container. The method may include heating aqueous antiseptic solution contained within a container or ampoule to a certain predetermined temperature and maintaining the temperature for a certain amount of predetermined time sufficient to sterilize the solution while maintaining sufficient purity of the antiseptic solution to comply with regulatory requirements. The antimicrobial efficacy directly relates to the purity of the antiseptic solution. Generally, when the purity of the antiseptic molecules is too low, the solution is not as effective in serving the function of an antimicrobial solution. Furthermore, higher levels of impurities within an antiseptic solution can have a deleterious impact on patient health.

The container is preferably a self-contained structure, formed of a material suitable for containing the antiseptic solution. In an aspect, the container may be made of a frangible material such that upon application of sufficient force the container fractures. For example, the material may comprise plastic or glass. The terms "container" and "ampoule" are used interchangeably herein. The wall of the container may have a thickness sufficient to withstand the sterilization process, transport, and storage. When the container is frangible, the material and thickness may also be sufficient to allow the container to be fractured upon the application of localized pressure. The thickness range may vary depending on the container size. Example thicknesses for glass or plastic containers include from about 0.15 mm to about 0.45 mm. In another example aspect, the container may comprise a non-frangible material, such as a metal (steel, aluminum, etc.) or such as a pouch comprising or consisting of a polymeric and/or foil material capable of withstanding the sterilization process. For example, the container may be a retort-like foil pouch having a composite material of polymeric and foil. An example thickness of the pouch may be about 0.002 inches to 0.010 inches.

While antiseptic solutions are of particular focus herein, the container may alternatively contain medicaments, chemical compositions, cleansing agents, cosmetics, or the like. For example, the container may be filled with antiseptic compositions (e.g., compositions comprising one or more antiseptic molecules), preferably an antimicrobial liquid or gel composition. For example, the antiseptic solution may contain non-active ingredients/agents with functions that include moisturizing, skin smoothing, visualization, solubility, stability, viscosity, wetting, etc.

In an aspect of the present invention, the antiseptic solution is aqueous. That is, the solvent of the solution is primarily water. As used herein, aqueous means at least about 50% v/v water, more preferably at least about 60% v/v water, more preferably at least about 70% v/v water, more preferably at least about 80% v/v water, more preferably at least about 90% v/v water, more preferably at least about 95% v/v, up to 100% v/v water. When the solution is less than 100% v/v water, the remaining volume may include one or more additional solvents, for example, alcoholic solvents. Example alcoholic solvents include ethanol, isopropanol, and n-propanol. For example, the solution may contain less than about 50% v/v, more preferably less than about 40% v/v, more preferably less than about 30% v/v, more preferably less than about 20% v/v, more preferably less than about 10% v/v, down to 0% v/v alcohol. A preferred alcohol may be isopropanol.

The container may contain antiseptic solution of a sufficient amount, sufficient concentration, and sufficient purity to be applied to a desired surface and have an antimicrobial effect on the desired surface. In one aspect, the desired surface is a patient's skin. It will be appreciated that the amount of antiseptic solution may vary. In one aspect the amount of antiseptic solution may be 0.01-100 mL of antiseptic. More preferably, the amount of antiseptic solution needed may be about 0.5-60 mL and still preferably may be about 0.5-30 mL. Examples include 0.67, 1, 1.5, 3, 10.5, 25 and 26 mL of antiseptic. In a situation where a larger amount of solution is desired, e.g., 26 mL, multiple smaller containers may be implemented in a single applicator (e.g., two 13 mL containers).

Suitable antiseptic molecules include bis-(dihydropyridinyl)-decane derivatives (e.g. octenidine salts) and/or biguanides (e.g., chlorhexidine salts). As used herein, the term "derivative" refers to a) a chemical substance that is related structurally to a first chemical substance and derivable from it; b) a compound that is formed from a similar first compound or a compound that can be imagined to arise from another first compound, if one atom of the first compound is replaced with another atom or group of atoms; c) a compound derived or obtained from a parent compound and containing essential elements of the parent compound; or d) a chemical compound that may be produced from first compound of similar structure in one or more steps. Examples of biguanides/biguanide derivatives other than chlorhexidine/chlorhexidine salts include alexidine, alexidine salts, polyhexamide, polyhexamide salts, polyaminopropyl biguanide, polyaminopropyl biguanide salts, and other alkyl biguanides. Preferred antiseptic agents include octenidine salts, such as octenidine dihydrochloride (a bis-(dihydropyridinyl)-decane derivative and a cationic surfactant), and chlorhexidine salts, such as chlorhexidine gluconate (a cationic biguanide). The concentration of the antiseptic may vary depending on the specific antiseptic species used or the desired antimicrobial effect that is desired. For example, when using octenidine or an octenidine salt the concentration may vary from about 0.0001% w/v to about 2.0% w/v, more preferably from about 0.01% w/v to about 1.0% w/v, and still more preferably from about 0.1% w/v to about 0.6% w/v. When chlorhexidine or a chlorhexidine salt is used, the concentration may be from about 0.1% w/v to about 5.0% w/v, more preferably from about 0.5% w/v to about 3.0% w/v, and still more preferably about 1.0% w/v to about 2.0% w/v.

In an aspect, when a biguanide, e.g., chlorhexidine or a chlorhexidine salt, is used, the purity of the solution, when applied to the skin (e.g., after the sterilization method described herein), may be at least about 90% pure, more preferably at least about 93% pure, still more preferably at least about 95% pure. As used herein, purity means the percent concentration of antiseptic molecules in solution relative to the total concentration of antiseptic molecules plus concentration of substances that are derived from or related to the antiseptic molecule. For example, a 95% pure antiseptic solution means that if there are 100 molecules that are either antiseptic molecules or molecules derived from or related to the antiseptic molecule, 95 of the molecules are the antiseptic molecule and 5 of those molecules are derived from or related to the antiseptic molecule. These molecules derived from or relating to the antiseptic molecule have reduced or no antimicrobial activity. Thus, a lower purity solution will have lower antimicrobial efficacy as fewer of the target antiseptic molecules are delivered to the patient's skin. Further, a lower purity solution will not comply with regulatory requirements. By measuring the concentration of antiseptic molecules in solution as compared to concentration of antiseptic molecules and molecules derived from or related to the antiseptic molecule, one can determine the purity of the solution and whether the purity is sufficient to comply with regulatory requirements.

In a preferred aspect, the antiseptic solution provided in the container comprises, consists essentially of, or consists of water as the only solvent and about 2.0% w/v antiseptic molecules. In a preferred aspect the antiseptic molecule may be chlorhexidine gluconate.

It has been found that when the aqueous antiseptic solution within the container is brought to a particular temperature and maintained at that temperature for a particular amount of time, the solution is sufficiently sterilized while maintaining sufficient antimicrobial efficacy as an antiseptic and while satisfying regulatory requirements. In an aspect of the present invention, the antiseptic solution may be brought to a temperature (also referred to herein as the "sterilization temperature") from about 100° C. to about 140° C., more preferably about 110° C. to about 130° C., and still more preferably about 115° C. to about 125° C.

As used herein, the term "predetermined sterilization time" means the length of time at which the solution is at the sterilization temperature. That is, the "sterilization time" does not include the time it takes for a solution to reach the sterilization temperature (i.e., does not include "ramp up" time) and also does not include the time it takes for the solution to return to the temperature the solution was at prior to the heating (i.e., does not include "cool down" time). The time it takes for the temperature of the solution to reach the sterilization temperature is referred herein as the "ramp up" time and the time to return to the starting temperature is referred herein as the "cool down" time. As used herein, the term "predetermined sterilization temperature" means the temperature or temperature range that the solution reaches and maintains during the sterilization time, independent of the starting temperature of the solution. For purposes of illustration only, a sterilization time of 60 minutes and a sterilization temperature of 110° C. for a solution starting at 21° C. would mean that the period of time starting from the moment the solution reaches 110° C. and ending the moment the solution falls below 110° C. during the beginning of the cool down process is 60 minutes. Thus, the time it takes from the solution to rise from 21° C. to 110° C. (i.e., ramp-up time) and the time it takes for the solution to return to 21° C. (i.e., cool-down time) is not included in the sterilization time.

The predetermined sterilization time and sterilization temperature provided herein generally assume the thermal exposure during the ramp-up and the cool-down does not contribute to the sterilization of the drug product as on a small scale these processes can be considered instantaneous. However, on a commercial scale, the time spent heating the product up will contribute to the overall lethality of the sterilization process, allowing the steady-state sterilization time to be decreased. When the ramp-up and cool-down contributions to the cycle are applied, the sterilization of the drug product can be described by the F-value calculated for each predetermined sterilization time and sterilization temperature using the following equation (see "Laboratory Manual for Food Canners and Processors", Vol. 1, AVI Publishing Co., Westport, Conn., 1968):

$$F = \Delta t \sum 10^{\frac{T-T_s}{z}}$$

where:

T is the temperature of the sterilized product at a particular time t.

Δt is the time interval between subsequent measurements of T.

Ts=the target sterilization temperature z=a temperature coefficient, normally assumed to be equal to 10° C., but calculable for specific microorganisms and therefore a variable For the purposes for illustration only, a sterilization temperature of 121° C. with a predetermined sterilization time of 6 minutes (i.e. ramp-up and cool-down do not contribute to the sterilization of the drug product) corresponds to a minimum F-value of 15 minutes at 121° C. ($F_{121}$) in order to sterilize the drug product. This minimum required F-value can be used to quantify a process in which the ramp-up and cool-down do contribute to the sterilization of the drug product. In such a process, the contribution for the ramp-up and cool-down on the minimum required F-value can be calculated. If during a sterilization cycle defined by an $F_{121}$=15 minutes a temperature of 121° C. is not reached, the cycle parameters could still be met per the calculation of $F_{121}$ as a summation of thermal input during the actual cycle.

It has been found that combinations of sterilization temperature and sterilization time can be selected to provide a sterilized aqueous antiseptic solution having sufficient purity to comply with regulatory requirements when used as an antiseptic. For example, for a sterilization temperature of about 100° C., the sterilization time may be at least about 20 minutes to about 33 hours. For a sterilization temperature of about 110° C., the sterilization time may be at least about 6 minutes and up to about 11 hours. For a sterilization temperature of about 115° C., the sterilization time may be at least about 3.5 minutes to about 6 hours. For a sterilization temperature of about 125° C., the sterilization time may be at least about 1 minute and up to about 2 hours. In an aspect of the present invention, the above example sterilization temperatures and sterilization times may be applied to an antiseptic solution comprising about 100% v/v water and about 2.0% w/v chlorhexidine gluconate or other antiseptic solutions described above.

It has been found that heating the antiseptic solution contained in the container to the above sterilization temperatures and maintaining the temperature for the above sterilization times, sufficiently sterilizes the solution, while maintaining sufficient purity to comply with regulatory requirements. The amount of degradation of the antiseptic molecule can be quantified by measuring the initial purity of antiseptic solution prior to the ramp up time (i.e., prior to the process of bringing the solution up to the sterilization temperature) and measuring the post-sterilized purity of antiseptic solution after the cool down time (i.e., after the antiseptic solution returns to the temperature the solution was at prior to the process of bringing the solution up to the sterilization temperature). Thus, as used herein, the "initial purity" is the purity prior to ramp up and "post-sterilization purity" is the purity of the solution after cool down. In an aspect of the present invention, the initial purity of the antiseptic solution, e.g., chlorhexidine gluconate, may be at least about 90%, preferably at least about 93%, and more preferably at least about 95%. The meaning of purity is provided above. The resulting post-sterilized solution is found to have sufficient purity to provide the desired antimicrobial efficacy as an antiseptic and to comply with regulatory requirements.

In an example aspect, it has been found that chlorhexidine gluconate molecules degrade into one or more the following molecules when heat treated: N-[[6-[[[(4-chlorophenyl)carbamimidoyl]carbamimidoyl]-amino]hexyl]carbamimidoyl] urea, N-(4-chlorophenyl)guanidine, N-(4-chlorophenyl)

urea, 1-(6-aminohexyl)-5-(4-chlorophenyl) biguanide, N-(4-chlorophenyl)-N'-[[6-[[[(4-chlorophenyl)carbamimidoyl]carbamimidoyl] amino]hexyl]carbamimidoyl]urea, 1-(4-chlorophenyl)-5-[6-[[(phenylcarbamimidoyl)carbamimidoyl]amino]hexyl]biguanide, 1-[6-(carbamimidoylamino)hexyl]-5-(4-chlorophenyl)-biguanide, and 4-chloroaniline. Thus, in an example aspect, the purity of the solution can be determined by comparing the amount of chlorhexidine gluconate to all of the above-listed chlorhexidine gluconate related substances. However, it should be noted that the above list is not exhaustive. One having ordinary skill in the art would be able to determine which molecules are degradants of the antiseptic molecule after the sterilization process.

As noted above, the purity of the antiseptic solution after the heating has been terminated and when the solution has returned to the temperature the solution was at prior to the process of bringing the solution up to the sterilization temperature (for example ambient temperature) is referred herein as the post-sterilization purity. As noted above, the post-sterilization purity is preferably measured when the antiseptic solution has cooled because degradation may occur during cooling. In an aspect of the present invention, by selecting an appropriate combination of sterilization temperature and sterilization time, the post-sterilization purity may be maintained relatively close to the initial purity, while still being sterile. In particular, the combination of sterilization temperature and sterilization time are chosen such that the percentage point change in purity from the initial purity to the post-sterilization purity is at most about 8%, more preferably at most about 5%, more preferably at most about 4%, and most preferably at most about 3%. It should be understood that the percentage point change refers to the absolute percentage point difference between the initial purity and the post-sterilization purity. For example, a change in initial purity of 95% to a post-sterilization purity of 90% is a percentage point change of 5%.

In addition to maintaining a sufficient purity, it has been found that the proper combination of sterilization temperature and sterilization time can be selected such that the solution is sterile. As used herein, sterile means "7 day sterility" as tested following the procedures described in U.S. Pharmacopeial Convention (USP) Chapter 55 "Biological Indicators—Resistance Performance Tests," USP 36; Official from May 1, 2013. Sterile also means completely free of microbes, immediately following sterilization. In an aspect, *Bacillus subtilis* may be used as a test microbe. Thus, in an aspect, a sterile solution would have no growth of *Bacillus subtilis* shown by the '7 day sterility' testing described above. In another aspect, a solution inoculated with *Bacillus subtilis* would be completely free of viable *Bacillus subtilis* immediately following the sterilization method.

In another aspect of the present invention, it was found that the inventive method has a sterility assurance level (SAL) of at least about $10^{-6}$ under particular combination of sterilization temperature and sterilization time. SAL is a measurement of probability of a microorganism occurring on an item following a sterilization procedure. A SAL of $10^{-6}$ means there is a 1 in 1,000,000 chance of a viable microorganism occurring in a sterilized product. Thus, the SAL measures the probability of a sterilization method resulting in a non-sterilized product. The calculation to determine SAL is described in more detail in the below examples. For example, it has been found that a method of exposing the aqueous antiseptic solution to a temperature of 105° C. for about 11 minutes, a temperature of 115° C. for about 2.3 minutes, or 121° C. for about 1.8 minutes would each have a SAL of at least $10^{-6}$ (i.e., a 1/1,000,000 chance that a viable microbe will be present in a sterilized solution).

As noted above, after the sterilization time ends, the solution may be cooled. For example, it may take about 10 to about 40 minutes to cool the antiseptic solution following the sterilization time. The time can be shortened using a cooling device. This additional time correlates with the particular sterilization temperature. For examples, a higher sterilization temperature (e.g., 125° C.) as compared to a lower sterilization (e.g., 100° C.) would take longer to return to room temperature after sterilization. Thus, the overall processing time, including cool down, may include an additional about 10 to about 20 minutes longer than the sterilization time.

It is within the scope of the invention that any machine capable of heating the antiseptic solution to the sterilization temperature and maintaining the solution at the sterilization temperature for the sterilization time may be used, while preferably limiting the ramp up time. Example equipment may include a water bath, oil bath, autoclave, convection oven, cascading water sterilizer, and the like. When using the cascading water sterilizer the ramp up time may be about 15 minutes, while the cool down time may be about 25 minutes. The cascading water sterilizer provides a constant stream of water which heats the solution to the sterilization temperature, maintains the sterilization temperature over the entirety of the sterilization time, and finally cools the solution.

As provided above, example combinations of sterilization time and sterilization temperature that provide a sterilized solution with sufficient purity to satisfy Regulatory requirements are as follows: the sterilization temperature may be about 100° C. and the sterilization time may be from about 20 minutes to about 33 hours; the sterilization temperature may be about 110° C. and the sterilization time may be at least about 6 minutes and up to about 11 hours; the sterilization temperature may be about 115° C. and the sterilization time may be at least about 3.5 minutes and up to about 6 hours; the sterilization temperature may be about 125° C. and the sterilization time may be at least about 1 minute and up to about 2 hours.

The sterile aqueous solution, after undertaking the above-described sterilization process, may be implemented in a variety of situations. For example, the original container in which the solution was sterilized may be placed into an antiseptic applicator. For example, the sterile solution in the original container may be placed within a multi-product kit, or a subcomponent of another final product.

Examples

A sample of aqueous antiseptic solution of 100% v/v water and 2.0% w/v chlorhexidine gluconate contained in a glass ampoule was tested in each of the following examples. The below experiments were performed by heating the indicated type of bath (e.g., water or oil) to the temperature indicated (e.g., 70° C.-114° C.). The solution had the initial purity indicated and the purity was tested at the times indicated in the tables. The purity percent values listed in the tables are the absolute purity of the chlorhexidine gluconate after heat treatment and cooling to ambient temperature. Each temperature was tested in duplicate. The Δpurity percent values are the percentage point change relative to the baseline purity. For example, in Table 1, a water bath was heated to 70° C. and a solution having 98.95% purity was tested. At 8 hours the purity of chlorhexidine gluconate solution was 98.92%, which is a 0.03% percentage point change from the initial purity of 98.95%.

Experiment #1

TABLE 1

70° C., Initial Purity 98.95%, water bath

| | Time (hours) | | | | |
|---|---|---|---|---|---|
| | 0 | 1 | 3 | 8 | 25 | 48 |
| Purity (%) | 98.95 | 98.94 | 98.94 | 98.92 | 98.78 | 98.64 |
| ΔPurity (%) | N/A | 0.01 | 0.01 | 0.03 | 0.16 | 0.30 |

TABLE 2

90° C., Initial Purity 98.95%, water bath

| | Time (hours) | | | | |
|---|---|---|---|---|---|
| | 0 | 0.5 | 1 | 2 | 4 |
| Purity (%) | 98.95 | 98.91 | 98.90 | 98.85 | 98.66 |
| ΔPurity (%) | N/A | 0.03 | 0.04 | 0.10 | 0.29 |

TABLE 3

105° C., Initial Purity 98.95%, oil bath

| | Time (hours) | | | | |
|---|---|---|---|---|---|
| | 0 | 0.25 | 0.5 | 1.0 | 1.5 |
| Purity (%) | 98.95 | 98.92 | 98.72 | 98.54 | 98.37 |
| ΔPurity (%) | N/A | 0.03 | 0.23 | 0.400.41 | 0.58 |

TABLE 4

114° C., Initial Purity 98.95%, oil bath

| | Time (hours) | | | | |
|---|---|---|---|---|---|
| | 0 | 0.25 | 0.5 | 1.0 | 1.5 |
| Purity (%) | 98.95 | 98.69 | 98.46 | 97.71 | 97.19 |
| ΔPurity (%) | N/A | 0.26 | 0.49 | 1.24 | 1.75 |

Experiment #2

TABLE 5

70° C., Initial Purity 99.24%, water bath

| | Time (hours) | | | | |
|---|---|---|---|---|---|
| | 0 | 1 | 3 | 8 | 25 | 48 |
| Purity (%) | 99.24 | 99.24 | 99.23 | 99.19 | 99.10 | 98.97 |
| ΔPurity (%) | N/A | −0.01 | 0.00 | 0.05 | 0.14 | 0.27 |

TABLE 6

90° C., Initial Purity 99.24%, water bath

| | Time (hours) | | | | |
|---|---|---|---|---|---|
| | 0 | 0.5 | 1 | 2 | 4 |
| Purity (%) | 99.24 | 99.21 | 99.19 | 99.13 | 98.96 |
| ΔPurity (%) | N/A | 0.03 | 0.05 | 0.11 | 0.28 |

TABLE 7

105° C., Initial Purity 99.24%, oil bath

| | Time (hours) | | | | |
|---|---|---|---|---|---|
| | 0 | 0.25 | 0.5 | 1.0 | 1.5 |
| Purity (%) | 99.24 | 99.18 | 99.10 | 98.85 | 98.58 |
| ΔPurity (%) | N/A | 0.06 | 0.14 | 0.39 | 0.66 |

TABLE 8

114° C., Initial Purity 99.24%, oil bath

| | Time (hours) | | | | |
|---|---|---|---|---|---|
| | 0 | 0.25 | 0.5 | 1.0 | 1.5 |
| Purity (%) | 99.24 | 99.05 | 98.78 | 98.01 | 97.42 |
| ΔPurity (%) | N/A | 0.19 | 0.45 | 1.23 | 1.81 |

The above data was then used to prepare an Arrhenius equation using the standard method in the art. The use of an Arrhenius equation is a well-known and accepted method of modeling temperature dependence on reaction rate. Using the Arrhenius equation, the following predicted values for purity were obtained.

TABLE 9

Predicted Purity Using Arrhenius Equation

| Sterilization Temperature | Maximum Sterilization Time to Maintain a Specified Purity Change (hr) | | |
|---|---|---|---|
| (° C.) | 3% | 5% | 8% |
| 100 | 12.21 | 20.36 | 32.57 |
| 101 | 10.92 | 18.20 | 29.11 |
| 102 | 9.76 | 16.27 | 26.03 |
| 103 | 8.74 | 14.56 | 23.30 |
| 104 | 7.82 | 13.04 | 20.86 |
| 105 | 7.01 | 11.68 | 18.69 |
| 106 | 6.28 | 10.47 | 16.75 |
| 107 | 5.63 | 9.39 | 15.02 |
| 108 | 5.06 | 8.43 | 13.48 |
| 109 | 4.54 | 7.57 | 12.11 |
| 110 | 4.08 | 6.80 | 10.88 |
| 111 | 3.67 | 6.11 | 9.78 |
| 112 | 3.30 | 5.50 | 8.79 |
| 113 | 2.97 | 4.95 | 7.91 |
| 114 | 2.67 | 4.45 | 7.13 |
| 115 | 2.41 | 4.01 | 6.42 |
| 116 | 2.17 | 3.62 | 5.79 |
| 117 | 1.96 | 3.26 | 5.22 |
| 118 | 1.77 | 2.94 | 4.71 |
| 119 | 1.59 | 2.66 | 4.25 |
| 120 | 1.44 | 2.40 | 3.84 |
| 121 | 1.30 | 2.17 | 3.47 |
| 122 | 1.18 | 1.96 | 3.14 |

TABLE 9-continued

Predicted Purity Using Arrhenius Equation

| Sterilization Temperature (° C.) | Maximum Sterilization Time to Maintain a Specified Purity Change (hr) | | |
|---|---|---|---|
| | 3% | 5% | 8% |
| 123 | 1.06 | 1.77 | 2.84 |
| 124 | 0.96 | 1.61 | 2.57 |
| 125 | 0.87 | 1.45 | 2.33 |

The measured impact of various sterilization temperatures and sterilization times on the characteristics of the antiseptic are shown below. Table 10 summarizes the change in % purity for the chlorhexidine gluconate after exposure to various sterilization temperatures and sterilization times. The percent change in purity is made by comparing the purity of solution prior to the ramp up time (i.e., prior to the process of bringing the solution up to the sterilization temperature) with the purity of solution after the cool down time (i.e., after the solution returns ambient temperature). The 'X', 'Y' and 'Z' indicate that the sterilization temperature and sterilization time would result in a change of purity of not more than 3%, 5% and 8%, respectively.

TABLE 10

Effect of Heat and Temperature on Chemical Stability

| Sterilization Temp (° C.) | Sterilization Time (hours) | | | | | | | | | | | |
|---|---|---|---|---|---|---|---|---|---|---|---|---|
| | 0.5 | 1 | 2 | 3 | 4 | 6 | 10 | 15 | 20 | 25 | 30 | 35 |
| 100 | | | | | | | X | Y | Y | Z | Z | |
| 105 | | | | | | X | Y | Z | | | | |
| 110 | | | | | X | Y | Z | | | | | |
| 115 | | | X | X | Y | Z | | | | | | |
| 120 | | X | Y | Z | | | | | | | | |
| 125 | X | Y | Z | | | | | | | | | |

KEY:
X = the solution had a change in purity of not more than 3%
Y = the solution had a change in purity of not more than 5%
Z = the solution had a change in purity of not more than 8%

The same can be done for other threshold values (e.g., changes in purity below or higher than 8%, such as 2%, 4%, and 6%).

In addition to above testing, further testing was conducted to determine at what time the Sterility Assurance Level (SAL) of $10^{-6}$ can be reached at a certain temperature. The USP 55 "Biological Indicators—Resistance Performance Tests" procedures were followed to determine the SAL. Greater than or equal to 1,000,000 test spores of *Bacillus subtilis*, but less than 10,000,000, were inserted into a 5 mL sample of an aqueous solution comprising 2.0% w/v chlorhexidine gluconate in 100% v/v water. The samples were tested at 105° C., 115° C., and 121° C. for various times. The results were as follows:

TABLE 11

Microbiological Testing at 105° C.

| Dilution | Exposure Time (minutes) | | | | | | | | | |
|---|---|---|---|---|---|---|---|---|---|---|
| | 0 CFU Count | | 2 CFU Count | | 4 CFU Count | | 6 CFU Count | | 8 CFU Count | |
| 2 (1/50) | — | — | — | — | — | — | — | — | — | — |
| 1/50 | — | — | — | — | — | — | 13 | 18 | 4 | 5 |
| 1/500 | — | — | — | — | 23 | 21 | 3 | 2 | 2 | 1 |
| 1/5,000 | — | — | 218 | 239 | 3 | 3 | — | — | 1 | 1 |
| 1/50,000 | TNTC | TNTC | 44 | 21 | 0 | 0 | — | — | — | — |
| 1/2 (1/50,000) | 216 | 268 | — | — | — | — | — | — | — | — |

| | Exposure Time (minutes) | | | | |
|---|---|---|---|---|---|
| | 0 Population | 2 Population | 4 Population | 6 Population | 8 Population |
| Four Ampoules | $2.42 \times 10^7$ | $1.38 \times 10^6$ | $1.10 \times 10^4$ | $7.75 \times 10^2$ | $1.99 \times 10^3$ |
| One Ampoule | $6.1 \times 10^6$ | $3.5 \times 10^5$ | $2.8 \times 10^3$ | $1.9 \times 10^2$ | $5.0 \times 10^2$ |

TNTC = Too Numerous to Count

TABLE 12

Microbiological Testing at 115° C.

| Dilution | Exposure Time (minutes) | | | | | | | | | |
|---|---|---|---|---|---|---|---|---|---|---|
| | 0 CFU Count | | 0.5 CFU Count | | 1 CFU Count | | 1.5 CFU Count | | 2 CFU Count | |
| 2 (1/50) | — | — | — | — | — | — | — | — | — | — |
| 1/50 | — | — | — | — | — | — | TNTC | TNTC | 0 | 2 |
| 1/500 | — | — | — | — | TNTC | TNTC | 249 | 231 | 0 | 0 |
| 1/5,000 | — | — | TNTC | TNTC | 93 | 107 | — | — | 0 | 0 |

TABLE 12-continued

| | | | | | Microbiological Testing at 115° C. | | | | | |
|---|---|---|---|---|---|---|---|---|---|---|
| 1/50,000 | TNTC | TNTC | 117 | 131 | 7 | 11 | — | — | — | — |
| 1/2 (1/50,000) | 216 | 268 | — | — | — | — | — | — | — | — |

| | Exposure Time (minutes) | | | | |
|---|---|---|---|---|---|
| | 0 Population | 0.5 Population | 1 Population | 1.5 Population | 2 Population |
| Four Ampoules | $2.42 \times 10^7$ | $6.2 \times 10^6$ | $5.00 \times 10^5$ | $1.20 \times 10^5$ | $5.00 \times 10^1$ |
| One Ampoule | $6.1 \times 10^6$ | $1.6 \times 10^6$ | $1.3 \times 10^5$ | $3.0 \times 10^4$ | $1.3 \times 10^1$ |

TNTC = Too Numerous to Count

TABLE 13

| | Microbiological Testing at 121° C. | | | | | | | | | |
|---|---|---|---|---|---|---|---|---|---|---|
| | Exposure Time (minutes) | | | | | | | | | |
| | 0 | | 0.5 | | 1 | | 1.5 | | 2 | |
| Dilution | CFU Count | | CFU Count | | CFU Count | | CFU Count | | CFU Count | |
| 2 (1/50) | — | — | — | — | — | — | 2 | 0 | 0 | 2 |
| 1/50 | — | — | — | — | 60 | 66 | 1 | 0 | 0 | 1 |
| 1/500 | — | — | TNTC | TNTC | 11 | 21 | — | — | — | — |
| 1/5,000 | — | — | TNTC | TNTC | 2 | 2 | — | — | — | — |
| 1/50,000 | TNTC | TNTC | 51 | 60 | — | — | — | — | — | — |
| 1/2 (1/50,000) | 216 | 268 | — | — | — | — | — | — | — | — |

| | Exposure Time (minutes) | | | | |
|---|---|---|---|---|---|
| | 0 Population | 0.5 Population | 1 Population | 1.5 Population | 2 Population |
| Four Ampoules | $2.42 \times 10^7$ | $2.78 \times 10^6$ | $3.15 \times 10^3$ | $2.50 \times 10^1$ | $2.50 \times 10^1$ |
| One Ampoule | $6.1 \times 10^6$ | $6.9 \times 10^5$ | $7.9 \times 10^2$ | $6.3 \times 10^0$ | $6.3 \times 10^0$ |

TNTC = Too Numerous to Count

The above data was then used to calculate the "D-values," in accordance with USP 55 procedures. The term D-value has the normal meaning as used in microbiology. Specifically, it refers to decimal reduction time and is the time required at a certain temperature to kill 90% of the organisms being studied. Thus after a colony is reduced by 1 D, only 10% of the original organisms remain, i.e., the population number has been reduced by one decimal place in the counting scheme. D-values can be calculated using the Survivor Curve Method, which is a data analysis known in the art (based on methods described in ISO 11138-1:2006). Applying the Survivor Curve Method to the above Table 11-13 data, the resulting D-values were calculated along with upper and lower confidence limits:

TABLE 14

| D-Values | |
|---|---|
| Temp (° C.) | D-value (min) |
| 105 | 1.75 |
| 115 | 0.38 |
| 121 | 0.29 |

The D-values can be used to calculate a sterility assurance Level (SAL) (see USP 55 procedures). SAL is a term used in microbiology to describe the probability of a single unit being non-sterile after it has been subjected to a sterilization process. A $10^{-6}$ SAL means there is a 1/1,000,000 chance that a single viable microbe will remain in sterilized items. The D-values were used to calculate the following time to achieve $10^{-6}$ SAL:

TABLE 15

| SAL $10^{-6}$ Time | |
|---|---|
| Temp (° C.) | Time to achieve SAL $10^{-6}$ (minutes) |
| 105 | 10.5 |
| 115 | 2.30 |
| 121 | 1.76 |

Thus, as indicated in Table 15, exposing the antiseptic solution to a temperature of 105° C. for about 10.5 minutes, a temperature of 115° C. for about 2.3 minutes, or 121° C. for about 1.8 minutes could each have a SAL of $10^{-6}$ (i.e., a 1/1,000,000 chance that a viable microbe will be present following the sterilization process).

Using standard mathematical modeling for the data presented in tables 11-13, an exponential predictive function having the following formula:

$$y = 2{,}122{,}036 \cdot e^{(-0.116x)} \tag{I}$$

where y is time in minutes and x is temperature in degrees Celsius. Thus, Formula (I) indicates at a given temperature the minimum time for achieving at least a $10^{-6}$ SAL. Using Formula (I), the following predictive data points were generated:

TABLE 16

Predictive SAL $10^{-6}$ Time

| Temp (° C.) | Time to achieve SAL $10^{-6}$ (min) |
|---|---|
| 100 | 20.03 |
| 101 | 17.84 |
| 102 | 15.89 |
| 103 | 14.15 |
| 104 | 12.61 |
| 105 | 11.23 |
| 106 | 10.00 |
| 107 | 8.91 |
| 108 | 7.94 |
| 109 | 7.07 |
| 110 | 6.30 |
| 111 | 5.61 |
| 112 | 5.00 |
| 113 | 4.45 |
| 114 | 3.96 |
| 115 | 3.53 |
| 116 | 3.14 |
| 117 | 2.80 |
| 118 | 2.50 |
| 119 | 2.22 |
| 120 | 1.98 |
| 121 | 1.76 |

FIG. 1 illustrates the sterilization times and temperatures fit to functions which capture the parameter space (time and temperature) to maintain a specific change in purity following the sterilization process (area between curves). The data points in FIG. 1 include data points from Table 9 and Table 16 above. The black squares represent the data points from 100° C. to 125° C. where the corresponding times were sterile. The following formula was fitted to the square data points from 100° C. to 125° C.:

$$T = 2.122 \times 10^6 \times e^{-0.116t} \text{ for } 100 \leq T \leq 125 \quad \text{(II)}$$

where T is the temperature in degrees Celsius and t is the time in minutes.

The data points found in Table 9 above were also plotted in FIG. 1. The black diamonds represent the data points from 100° C. to 125° C. where the corresponding times had at most a percent change in purity of 8%. The black triangles represent the data points from 100° C. to 125° C. where the corresponding times had at most a percent change in purity of 5%. The black circles represent data points from 100° C. to 125° C. where the corresponding times had at most a percent change in purity of 3%. The following formula was fitted to the black diamond data points (i.e. the points having at most 8% change in purity):

$$T = 7.341 \times 10^7 \times e^{-0.155t} \text{ for } 100 \leq T \leq 125 \quad \text{(III)}$$

The following formula was fitted to the black triangle data points (i.e., the points having at most 5% change in purity):

$$T = 4.588 \times 10^7 \times e^{-0.155t} \text{ for } 100 \leq T \leq 125 \quad \text{(IV)}$$

where T is the temperature in degrees Celsius and t is the time in minutes. The following formula was fitted to the black circle data points (i.e., the points having at most 3% change in purity):

$$T = 2.753 \times 10^7 \times e^{-0.155t} \text{ for } 100 \leq T \leq 125 \quad \text{(V)}$$

where T is the temperature in degrees Celsius and t is the time in minutes.

As can be seen in FIG. 1, the area bounded by the functions defined in Formula (II) and Formula (III), for temperatures between 100° C. to 125° C., represents temperature and time combinations that provide a sterile solution with at most a 8% change in purity. This area can thus be presented by subtracting Formula (III) from Formula (II)

$$T = 7.341 \times 10^7 \times e^{-0.155t} - 2.122 \times 10^6 \times e^{-0.116t} \text{ for } 100 \leq T \leq 125$$

where T is temperature in degrees Celsius and t is time in minutes.

As can be seen in FIG. 1, the area bounded by the functions defined in Formula (II) and Formula (IV), for temperatures between 100° C. to 125° C., represents temperature and time combinations that provide a sterile solution with at most a 5% change in purity. This area can thus be presented by the following relationship:

$$T = 4.588 \times 10^7 \times e^{-0.155t} - 2.122 \times 10^6 \times e^{-0.116t} \text{ for } 100 \leq T \leq 125$$

where T is temperature in degrees Celsius and t is time in minutes.

As can be seen in FIG. 1, the area bounded by the functions defined in Formula (II) and Formula (V), for temperatures between 100° C. to 125° C., represents temperature and time combinations that provide a sterile solution with at most a 3% change in purity. This area can thus be presented by the following relationship:

$$T = 2.753 \times 10^7 \times e^{-0.155t} - 2.122 \times 10^6 \times e^{-0.116t} \text{ for } 100 \leq T \leq 125$$

where x is temperature in degrees Celsius and y is time in minutes.

The above results, specifically, that an aqueous solution of 2% w/v chlorhexidine gluconate remains sufficiently pure after sterilization is surprising. Additional experiments were conducted where an aqueous solution having 100% v/v water and 2% w/v chlorhexidine gluconate was heated in sealed ampoules at 121° C. for various times. Comparison was made to an alcoholic solution of 2% w/v chlorhexidine gluconate, 70% v/v isopropyl alcohol, and the remainder water. The results indicated that the degradation rate of the aqueous 2% w/v chlorhexidine gluconate was significantly slower (13-18 fold) than the alcoholic 2% w/v chlorhexidine gluconate at 25° C. Previous studies have shown that the degradation rate of aqueous solution having 100% v/v water and 20% w/v chlorhexidine gluconate at 25° C. is nearly identical to the degradation rate of the alcoholic solution of 2% w/v chlorhexidine gluconate. Because the aqueous 20% w/v chlorhexidine gluconate had the same degradation rate as the alcoholic solution of 2% w/v chlorhexidine gluconate, one would expect the aqueous 2% w/v chlorhexidine gluconate to exhibit a similar degradation rate.

In order to predict if the differences in the extent of chlorhexidine gluconate degradation are inherent to the solutions and would exist at any time and temperature, an Arrhenius equation was established for aqueous 2% w/v chlorhexidine gluconate and an aqueous solution having 20% w/v chlorhexidine gluconate, alcoholic solution of 2% w/v chlorhexidine gluconate by monitoring the increase in total related substances with respect to time and temperature. Two different manufacturers (referred herein as Manufacture A and Manufacture B) of the aqueous 20% w/v chlorhexidine gluconate were tested. The two different supplied aqueous 20% w/v chlorhexidine gluconate were diluted with water to 2% w/v chlorhexidine gluconate for purposes of testing (i.e., remaining 100% v/v water).

Figure 2:
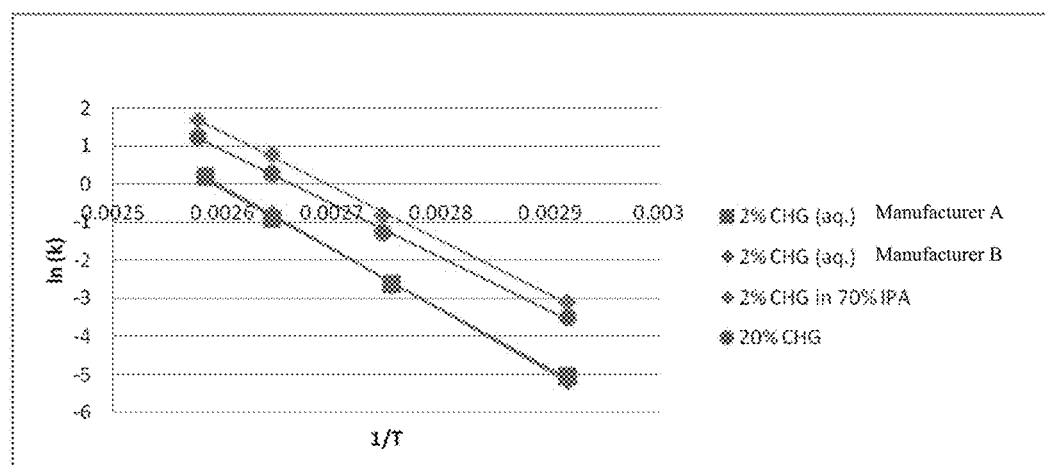
FIG. 2 is a graph of an Arrhenius Plot of various chlorhexidine gluconate formulations.

The Arrhenius equations for the two aqueous 2% w/v chlorhexidine gluconate were compared to the Arrhenius equations for aqueous 20% w/v chlorhexidine gluconate, and the alcoholic solution having 2% w/v chlorhexidine gluconate. The results are shown in FIG. 2. As shown in FIG. 2, the degradation rate of both aqueous 2% chlorhexidine gluconate solution from Manufacturer A and Manufacturer B is significantly slower than both the alcoholic 2% w/v chlorhexidine gluconate and the aqueous 20% w/v aqueous chlorhexidine gluconate. A prediction of the degradation rates at 25° C. for aqueous 2% w/v chlorhexidine gluconate in comparison to aqueous 20% w/v and alcoholic 2% w/v chlorhexidine gluconate are shown in Table 17 below.

TABLE 17

Total Related Substances Degradation Rate Predicted at 25° C.

| Formulation | Degradation Rate* (% TRS/mo) at 25° C. |
| --- | --- |
| 2% chlorhexidine gluconate (aq.) (Manufacturer A) | 0.00459 |
| 2% chlorhexidine gluconate (aq.) (Manufacturer B) | 0.00316 |
| 2% chlorhexidine gluconate in 70% | 0.0764 |
| 20% (aq.) chlorhexidine gluconate | 0.0549 |

*Values extrapolated from the corresponding Arrhenius equations

Further, as shown in FIG. 2 and Table 17, it was determined that the degradation rate for the alcoholic 2% w/v chlorhexidine gluconate is comparable to the aqueous 20% chlorhexidine gluconate at all temperatures.

The above-described degradation results are particularly surprising in view of further testing showing that the difference in degradation rate cannot be directly correlated with only one of the following factors: alcohol content, the difference in pH/apparent pH, and the amount of dilution.

Figure 3:
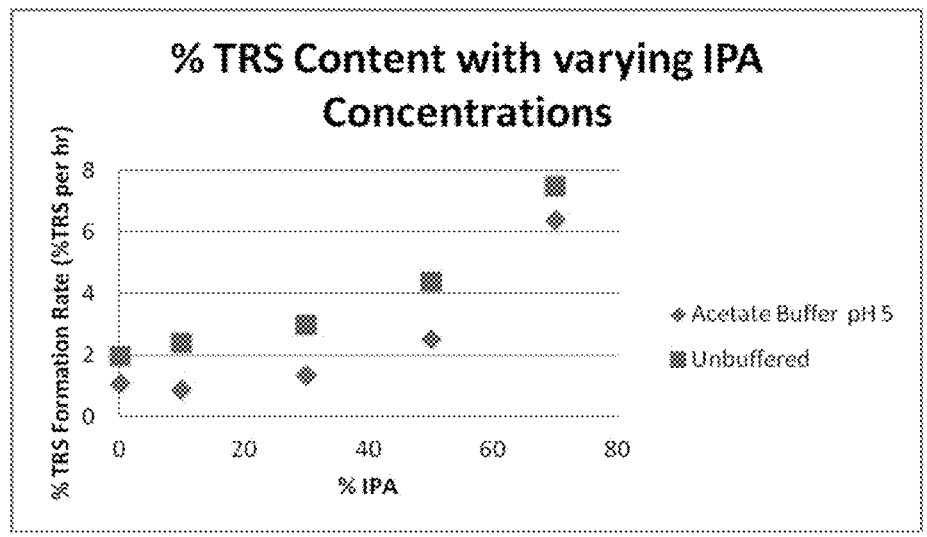
FIG. 3 is a graph of percent total related substances (% TRS) degradation rates of buffered and unbuffered 2% aqueous chlorhexidine gluconate formulation with various concentrations of isopropyl alcohol (IPA).

To investigate the effect of isopropyl alcohol on the degradation rate, formulations with increasing concentrations of isopropyl alcohol were prepared with either a non-buffered (water) or buffered system (50 mM acetate buffer pH about 5). A buffered system was used in addition to varying the isopropyl alcohol concentration in order to minimize the effect of differences in the solution's apparent pH when degrading the chlorhexidine gluconate formulations. The results, shown in FIG. 3, indicate that as the isopropyl alcohol concentration increases, the chlorhexidine gluconate degradation rate (increase in formation of total related substances (TRS)) also increases.

Figure 4:
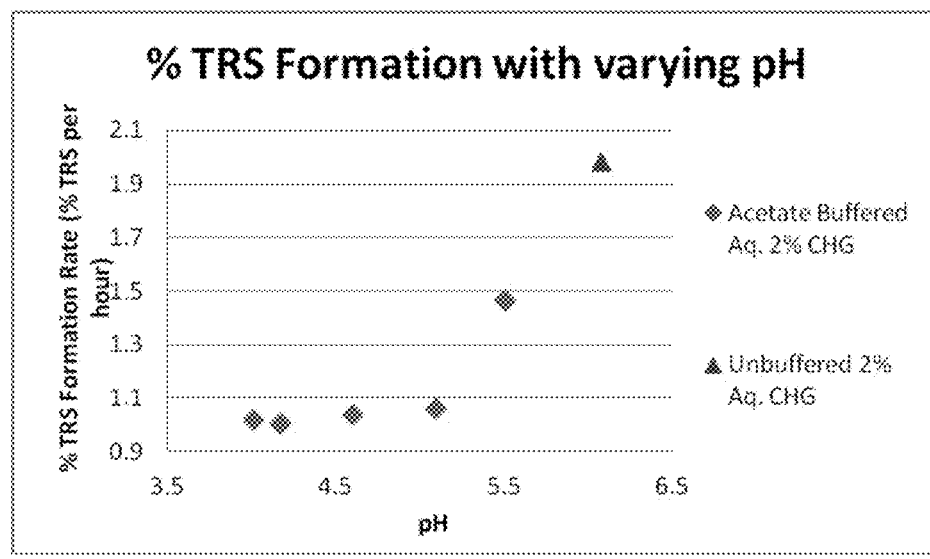
FIG. 4 is a graph of a pH rate profile of 2% aqueous chlorhexidine gluconate.

To determine the effect of pH on the degradation rate of chlorhexidine gluconate, aqueous 2% w/v chlorhexidine gluconate formulations were prepared at various pHs using an 50 mM acetate buffer (see FIG. 4). The chlorhexidine gluconate degradation rate is independent of pH, when the aqueous solution pH in the range of approximately 4.0-5.0. As the solution pH increases above pH 5, the chlorhexidine gluconate degradation rate also increases.

Dilution of aqueous 20% w/v chlorhexidine gluconate to achieve an aqueous 2% w/v chlorhexidine gluconate solution does not significantly impact the solution pH (A pH about 0.2 pH units). Further, when the chlorhexidine gluconate is diluted, the pH of the aqueous 2% w/v chlorhexidine gluconate solution (pH 6.4) is higher than that of aqueous 20% w/v chlorhexidine gluconate (pH 6.2). Thus, the differences in the observed degradation rates between aqueous 2% w/v chlorhexidine gluconate and aqueous 20% w/v chlorhexidine gluconate isn't a pH phenomenon based on the results shown in FIG. 4, where an increase in pH trends with an increase in degradation.

In summary, different mechanisms are governing the observed differences in degradation rates between the various chlorhexidine gluconate formulations described above. Thus, the observed lower degradation rate of aqueous 2% w/v chlorhexidine gluconate compared to alcohol solution of 2% w/v chlorhexidine gluconate, and aqueous 20% w/v chlorhexidine gluconate was surprising.

While aspects of the present invention have been described in connection with illustrative implementations, it will be understood by those skilled in the art that variations and modifications of the aspects described above may be made without departing from the scope hereof. Other variations will be apparent to those skilled in the art from a consideration of the specification or from a practice along the lines as disclosed herein.

The invention claimed is:

1. A method for sterilizing an aqueous antiseptic solution, the method comprising:
providing a container containing the aqueous antiseptic solution, the aqueous antiseptic solution comprising about 2.0% w/v chlorhexidine gluconate;
heating the aqueous antiseptic solution to a predetermined temperature, wherein the predetermined temperature is from about 100° C. to about 140° C.;
maintaining the aqueous antiseptic solution at the predetermined temperature for a predetermined time; and
terminating the heating of the aqueous antiseptic solution when the predetermined time expires,
wherein the predetermined temperature and the predetermined time are selected such that after terminating the heating, the aqueous antiseptic solution is sterile.

2. The method of claim 1,
wherein prior to heating, the aqueous antiseptic solution has an initial purity,
wherein after terminating the heating, the aqueous antiseptic solution has a post-sterilization purity, and
wherein the predetermined temperature and the predetermined time are selected such that the post-sterilization purity is at least about 90% and a percentage point change in purity from the initial purity to the post-sterilization purity of at most about 8%.

3. The method of claim 2, where the post-sterilization purity is at least about 93% and a percentage point change in purity from the initial purity to the post-sterilization purity of at most about 5%.

4. The method of claim 2, where the post-sterilization purity is at least about 95% and a percentage point change in purity from the initial purity to the post-sterilization purity of at most about 3%.

5. The method of claim 1, wherein the predetermined temperature is from about 110° C. to about 130° C.

6. The method of claim 1, wherein the predetermined temperature is from about 115° C. to about 125° C.

7. The method of claim 1, wherein the predetermined time is from about 20 minutes to about 33 hours.

8. The method of claim 1, wherein the predetermined time is from about 6 minutes to about 11 hours.

9. The method of claim 1, wherein the predetermined time is from about 1 minute to about 2 hours.

10. The method of claim 1, wherein the aqueous antiseptic solution comprises at least 50% v/v water.

11. The method of claim 1, wherein the aqueous antiseptic solution comprises at least 90% v/v water.

12. The method of claim 1, wherein after terminating the heating, the aqueous antiseptic solution is completely free of microbes.

13. The method of claim 1, wherein the aqueous antiseptic solution comprises from about 50% to about 100% v/v water.

14. The method of claim 1, wherein the aqueous antiseptic solution comprises about 100% v/v water.

15. The method of claim 1, wherein the aqueous antiseptic solution consists essentially of:
   chlorhexidine gluconate
   from about 50% to about 100% v/v water.

16. The method of claim 1, wherein the aqueous antiseptic solution consists essentially of:
   from about 65% to about 100% v/v water;
   chlorhexidine gluconate.

17. The method of claim 1, wherein the aqueous antiseptic solution consists essentially of:
   about 100% v/v water;
   chlorhexidine gluconate.

18. The method of claim 1, wherein the aqueous antiseptic solution consists of:
   about 75% to about 100% v/v water;
   chlorhexidine gluconate; and
   the remainder volume alcohol.

19. The method of claim 1, wherein the aqueous antiseptic solution comprises a non-active ingredient.

20. The method of claim 19, wherein the non-active ingredient is selected from the group consisting of a moisturizing agent, skin smoothing agent, a visualization agent, a solubility agent, a stability agent, a viscosity agent, and a wetting agent.

21. A sterile aqueous antiseptic solution prepared according to the method of claim 1.

* * * * *